(12) United States Patent
Gon et al.

(10) Patent No.: US 10,544,054 B2
(45) Date of Patent: Jan. 28, 2020

(54) METHOD FOR DETECTING AND CONTROLLING THE AMOUNT OF CATIONIC SPECIES IN A WATER STREAM

(71) Applicant: Ecolab USA Inc., St. Paul, MN (US)

(72) Inventors: Saugata Gon, Sugar Land, TX (US); Anoop Chengara, Aurora, IL (US)

(73) Assignee: ECOLAB USA INC., St. Paul, MN (US)

( * ) Notice: Subject to any disclaimer, the term of this patent is extended or adjusted under 35 U.S.C. 154(b) by 79 days.

(21) Appl. No.: 15/878,641

(22) Filed: Jan. 24, 2018

(65) Prior Publication Data
US 2018/0208489 A1 Jul. 26, 2018

(30) Foreign Application Priority Data
Jan. 25, 2017 (IN) .............................. 201721002824

(51) Int. Cl.
*C02F 1/68* (2006.01)
*G01N 33/18* (2006.01)
*G01N 21/64* (2006.01)
*C02F 1/52* (2006.01)
*C02F 1/50* (2006.01)
*C02F 103/10* (2006.01)

(52) U.S. Cl.
CPC ................. *C02F 1/68* (2013.01); *C02F 1/50* (2013.01); *C02F 1/5209* (2013.01); *C02F 1/5272* (2013.01); *G01N 21/643* (2013.01); *G01N 33/1813* (2013.01); *C02F 2103/10* (2013.01); *C02F 2303/08* (2013.01); *C02F 2303/18* (2013.01); *G01N 2021/6439* (2013.01)

(58) Field of Classification Search
None
See application file for complete search history.

(56) References Cited

U.S. PATENT DOCUMENTS

| 5,389,548 | A | 2/1995 | Hoots et al. |
| 5,413,719 | A | 5/1995 | Sivakumar et al. |
| 5,435,969 | A | 7/1995 | Hoots et al. |
| 5,645,799 | A | 7/1997 | Shah et al. |

FOREIGN PATENT DOCUMENTS

WO    WO 99/51817 A1    10/1999

OTHER PUBLICATIONS

Fagadar-Cosma, Eugenia et al., "UV-VIS and Fluorescence Spectra of Meso-Tetraphenylporphyrin and Meso-Tetrakis-(4-Methoxphenyl) Porphyrin in THF and THF-Water Systems. The influence of PH", XP055480725, *Rev. Chim.*, 58(5):451-455 (2007).
Staninski, Krzysztof, et al., "Emission spectroscopic properties of water soluble porphyrins in hydrogen peroxide chemiluminescence system withd-andf-electron metals", *Journal of Solid State Chemistry*, 171(1):208-211 (2003).

*Primary Examiner* — Richard C Gurtowski
(74) *Attorney, Agent, or Firm* — Eric D. Babych; Barnes & Thornburg LLP

(57) ABSTRACT

A method for detecting and controlling the amount of cationic species in a water stream in accordance with embodiments of the present disclosure is carried out by adding a solution containing a pre-determined quantity of a fluorescent tracer to the sample of water stream to obtain a solution comprising a complex. The fluorescence emission spectra of the solution is measured for detecting the presence or absence of the cationic species based on the attenuation and shift of the emission peak in the range of 640 nm to 655 nm.

14 Claims, 13 Drawing Sheets

METHOD FOR DETECTING AND CONTROLLING THE AMOUNT OF CATIONIC SPECIES IN A WATER STREAM

FIELD

The present disclosure relates to methods for detecting and controlling the amount of certain components, such as one or more cationic species, in a water stream.

BACKGROUND

Waste water streams generated from various industries, such as the paper and pulp industry, the textile industry and the polymer industry, contain unacceptable amounts of dissolved or suspended impurities. Cationic coagulants and flocculants are extensively used as treating agents for such waste water.

Residual cationic species in a water stream can cause fouling and environmental problems. Also, cationic species pose problems for processes like filtration, ion exchange, and reverse osmosis units.

In oil fields, waste water treatment has to be carried out for removing oil-in-water (OIW) reverse emulsions. Oil molecules often create a strong background fluorescent signal and thus pose a hurdle to the detection of cationic species.

In some instances, fluorescent tracers are added to waste water along with the treating agent. However, adding fluorescent tracers with the treating agent can itself be a challenge as the tracer may alter the properties of the treating agent and can further increase the production cost. The presence of residual fluorescent tracers in the treated water can also cause environmental issues.

SUMMARY

The present disclosure provides methods for detecting and controlling the amount of certain components, such as one or more cationic species, present in a water stream. In certain embodiments, the methods involve the use of a compound that acts as a tracer as well as a complexing agent. The tracer being fluorescent in nature, its emission, or absorbance pattern, may be used to detect the presence or the absence of a free cationic species, for example. Attenuation and shift of the emission peak in the range of 640 nm to 655 nm, for example, indicates the presence of free cationic species in the water stream. Based on the results of the emission spectra, the quantity of the cationic species can also be detected by either diluting the water sample or increasing the concentration of the quantity of the fluorescent tracer and then again measuring the emission spectra. The results obtained can be used to control the dosage of treatment chemicals, such as cationic coagulants and flocculants, in the treatment of water.

Further, after detection of the amount of the cationic species in the water sample, a predetermined quantity of an anionic neutralizer can be added to the main water stream to obtain the desirable threshold level of the cationic species in the water stream. The threshold level of the cationic species present in the water stream may vary depending upon the type of water stream. In some embodiments, the threshold level ranges from about 1 ppm to about 50 ppm.

In certain embodiments, the present disclosure provides methods for detecting and controlling an amount of a cationic species in a water stream. The methods comprise drawing a water sample from said water stream; adding a pre-determined quantity of at least one fluorescent tracer to said water sample to form a solution comprising a complex; measuring a fluorescence emission spectra of said complex in a range of about 500 nm to about 700 nm when excited at about 420 nm and detecting the presence or absence of the cationic species in the complex of said solution based on an attenuation of an emission peak and a shift of the emission peak in a range of about 640 nm to about 655 nm; detecting the quantity of the cationic species in said water sample: adding an amount of an anionic neutralizer proportional to the quantity of the cationic species detected in step (d) to said water stream to obtain a water stream with the desired level of the cationic species; and optionally repeating the steps (a) to (e) for controlling the amount of the cationic species in said water stream below a threshold level.

Certain embodiments of the present disclosure provide methods for detecting and controlling the amount of cationic species in a water stream in order to prevent fouling of equipment, such as a downstream water clarifier unit, or any other piece of equipment that may contact the water. Additional embodiments of the present disclosure provide methods for detecting and controlling the amount of one or more cationic species in a water stream, wherein the methods can be employed in an oil field water stream with negligible interference of oil in the fluorescent signals.

The foregoing has outlined rather broadly the features and technical advantages of the present disclosure in order that the detailed description that follows may be better understood. Additional features and advantages of the disclosure will be described hereinafter that form the subject of the claims of this application. It should be appreciated by those skilled in the art that the conception and the specific embodiments disclosed may be readily utilized as a basis for modifying or designing other embodiments for carrying out the same purposes of the present disclosure. It should also be realized by those skilled in the art that such equivalent embodiments do not depart from the spirit and scope of the disclosure as set forth in the appended claims.

BRIEF DESCRIPTION OF THE ACCOMPANYING DRAWING

DETAILED DESCRIPTION

Figure 1:
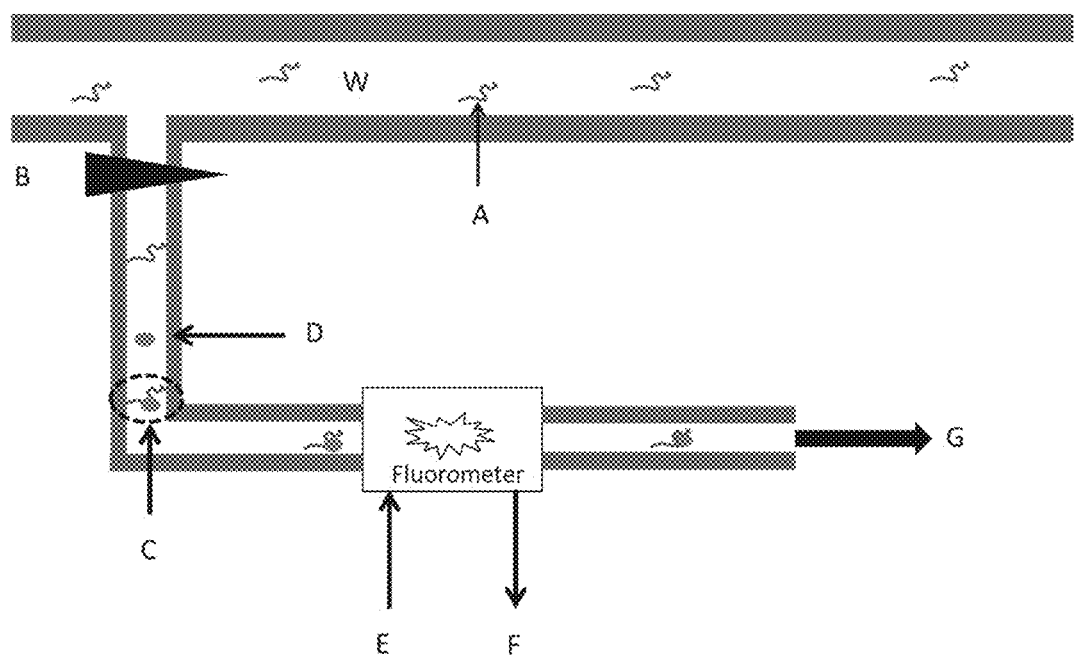
FIG. 1 illustrates a schematic representation of a side stream method and use of 4,4',4'',4'''-(Porphine-5,10,15,20-tetrayl) tetrakis (benzenesulfonic acid) (PTTBSA) for cationic residue detection.

As used in the present disclosure, the following terms are generally intended to have the meaning as set forth below, except to the extent that the context in which they are used indicates otherwise.

The expression 'CI' for the purpose of the present disclosure refers to corrosion inhibitor.

The expression 'OIW' for the purpose of the present disclosure refers to oil in water emulsion.

The expression 'OFC' for the purpose of the present disclosure refers to oil field chemicals.

The expression 'WPS' for the purpose of the present disclosure refers to water and process services.

The expression 'AC' for the purpose of the present disclosure refers to anionic coagulants.

The expression 'RO' for the purpose of the present disclosure refers to reverse osmosis.

The expression 'PTTBSA' for the purpose of the present disclosure refers to 4,4',4",4'''-(Porphine-5,10,15,20-tetrayl) tetrakis (benzenesulfonic acid).

The expression 'DADMAC/AcAm copolymer' for the purpose of the present disclosure refers to diallyldimethyl ammonium chloride acrylamide copolymer.

The expression 'DMAEA.BCQ' for the purpose of the present disclosure refers to dimethylaminoethylacrylate benzyl chloride quaternary.

The expression 'DMAEA.BCQ' for the purpose of the present disclosure refers to DMAEA.MCQ: dimethylaminoethylacrylate methyl chloride quaternary.

The expression 'target oil' for the purpose of the present disclosure refers to different concentration of oil in water emulsions.

The expression 'Milli-Q water' for the purpose of the present disclosure refers to ultrapure water of 'type 1' as defined by various authorities, such as ISO3696, American Chemical Society (ACS).

The expression 'cuvette' for the purpose of the present disclosure refers to a small tube of circular or square cross section, sealed at one end, made of plastic, glass, fused quartz (for UV light), and the like, and designed to hold samples for spectroscopic experiments.

Cationic species, such as coagulants, flocculants, water clarifiers, corrosion inhibitors and biocides, are used extensively for water treatment in various industries. However, such cationic species pose a problem for reverse osmosis membranes, ion exchange membranes, filtration units, and the like. Hence, the detection of such cationic species is desirable for the optimum functioning of various membranes used in water treatment facilities and for the release of the water into the environment.

In one embodiment, the present disclosure provides a method for detecting the amount of a cationic species present in a water stream.

In a step of the method, a sample of the water stream is obtained. The origin of the water stream is not limited and can be, for example, industrial waste water or oil-field waste water, which contains one or more cationic species. The cationic species in the water stream is not limited and can be a cationic water clarifiers, such as a coagulants and/or a flocculant, a biocide, a corrosion inhibitor, a polyamine residue, a polymer species, and any combination thereof, for example.

The step of obtaining a sample of a water stream can include a pre-step of treating the water stream using a treating agent, wherein the treating agent is at least one selected from the group consisting of biocides, flocculants, corrosion inhibitors, coagulants, and water clarifiers.

In another step, a solution containing a pre-determined quantity of at least one fluorescent tracer is added to the sample of water stream to obtain a solution containing complexes of the cationic species and fluorescent tracer. In certain embodiments, the fluorescent tracer is an anionic fluorescent dye. In some embodiments, the anionic fluorescent dye is PTTBSA. The amount of PTTBSA used for detecting the cationic species is not limited and in some embodiments, it ranges from about 5 ppb to about 10 ppb and includes any amount there between. While PTTBSA has been exemplified, any anionic fluorescent dye may be used. In some embodiments of the present disclosure, the ratio of the cationic species to the fluorescent tracer ranges from about 100:1 to 250:1, such as about 200:1. The complex obtained comprises a complex of the cationic species and the anionic fluorescent tracer.

The interaction of the fluorescent tracer with the cationic species and optionally other organics in the water alters the fluorescence intensity of the fluorescent tracer. The fluorescence intensity is dependent on the surface charge density of the cationic species and on the concentration of organics and the fluorescent tracer itself. The fluorescence shows either a steep decrease at a threshold residual product/solution (a solution containing a complex of cationic species and fluorescent tracer) concentration or a linear decrease with increasing residual product concentration. This change in the fluorescence condition with residual product concentration can be used to detect the amount of the cationic species concentration and thereby control its specified residual concentration in the water stream. The methods of the present disclosure can help avoid either under-dosing or overdosing the fluorescent tracer, the cationic coagulants, the cationic flocculants, and/or the anionic neutralizers, and they prevent fouling of components in fluid communication with the water.

A further method step includes measuring the fluorescence intensity of the formed complex. Fluorescence intensity may be measured by a spectrofluorometer using emission/absorbance spectra. The emission spectra of the fluorescent tracer are measured at a wavelength ranging from about 500 nm to about 700 nm, maintaining the excitation peak at about 420 nm in certain embodiments.

The step of measuring the fluorescence intensity may comprise a pre-step of correcting the baseline of the absorbance spectra to nullify the effect of spectral interfering components.

Fluorescence intensity increases with fluorescent tracer concentration in the absence of cationic species, but the attenuation of fluorescence signal by the cationic species is observed at all concentrations of the fluorescent tracer. In one embodiment, addition of about 0.005 ppm of fluorescent tracer (cationic species to fluorescent tracer ratio about 200:1) yielded significant attenuation. As such, this ratio may be chosen for cationic species detection.

The cationic species are detected by the presence or absence of an emission peak. The presence of cationic species in the solution is determined by attenuation of the emission peak ranging from about 635 nm to about 655 nm. As the fluorescent tracer (anionic fluorescent dye) attaches onto the cationic species, its emission peak near 640 nm, (when excited at about 420 nm) gets attenuated. The degree of attenuation is dependent on the morphology of the residual cationic species and their charge densities (as the polymer folds its surface charge density for changing their orientation, the morphology of the polymer may change). This attenuation of the fluorescent tracer emission spectra can be used as an index of residual cationic species detection.

The quantification of the cationic species present in the water stream can be done statistically by creating a calibration curve with a set of calibration solutions containing the target species in the relevant water stream in an increasing dosage and a predetermined quantity of tracer. In an additional step, the quantity of cationic species in the water stream can be determined by diluting the sample of water stream containing the cationic species and maintaining a pre-determined quantity of fluorescent tracer, or it may be determined by increasing the quantity of the fluorescent tracer and maintaining the concentration of cationic species in the sample of water stream.

The amount of cationic species is detected by measuring the fluorescence intensity of the water sample until the fluorescence intensity of the complex present in the water sample reaches a steady state. The detection of the quantity of the cationic species in the water sample can be carried out by any of the method given below.

In one method, detecting the quantity of the cationic species in the water sample is carried out by measuring the fluorescence intensity/fluorescence peak of water samples after mixing predetermined quantities of the fluorescent tracer in increasing mass of water in the sample to obtain mixtures, each mixture comprising a complex of fluorescent tracer and cationic species, and measuring the fluorescence intensity of the complex present in the mixture until the fluorescence intensity of the mixture reaches a steady state.

In another method, detecting the quantity of the cationic species in the water sample is carried out by measuring the fluorescence intensity/fluorescence peak of the water sample by mixing predetermined volumes of water samples with increasing quantities of fluorescent tracer to obtain mixtures, each mixture comprising a complex of fluorescent tracer and cationic species, and measuring the fluorescence intensity of the mixture (complex present in the mixture) until the fluorescence intensity of the mixture reaches a steady state.

Once the amount of cationic species present in the sample of water stream is determined, an optimum dosage of the anionic neutralizer may be determined in order to obtain the desired level of cationic species in the water stream. The optimum dosage can be selected by one of ordinary skill in the art depending at least in part on the amount of cationic species in the water.

The steps illustrated above for detecting and controlling the cationic species in the water stream may be repeated to obtain a water stream with cationic species below the desired threshold level.

Any known anionic neutralizers can be used for neutralizing the cationic species in the water stream. In some embodiments, the anionic neutralizers can be selected from the group consisting of coagulants and flocculants. In one exemplary embodiment, the anionic neutralizer is a dithiocarbamate.

The methods of the present disclosure have the advantage of effectively controlling the amount of fluorescent tracer and cationic species in water.

The method for detecting and controlling the amount of cationic species in a water stream in accordance with one embodiment of the present disclosure will now be described with reference to the accompanying drawings, which do not limit the scope and ambit of the disclosure. In FIG. 1, a water sample from a water stream (W) containing the cationic species (A) to be detected is obtained through a gate valve (B) as a side stream. A pre-determined amount of fluorescent tracer (D) is added to the side stream containing the cationic species, to obtain a solution containing a complex (C) of the fluorescent tracer and the cationic species. The emission spectrum of the solution comprising complex is maintained at an excitation peak of about 420 nm wavelength (E). The emission spectrum of the solution is measured at a wavelength ranging from about 500 nm to about 700 nm (F) using a spectrofluorometer. The emission spectra are analyzed by using a software program, for example, and the amount of cationic species present in the water sample is detected. The water sample containing the complex of cationic species and fluorescent tracer is sent for disposal (G) or may be recycled back to the water stream (W).

The fluorescence intensity was tested by a spectrofluorometer (HORIBA Jobin Yvon Fluromax-4 spectrofluorometer). Fluorescence spectra was measured by keeping Excitation wavelength: 420 nm, Slit width: 2.5 nm Emission spectra wavelength range: 500-700 nm, Slit width: 2.5 nm Detector setting: Detector type S (S1), measuring unit CPS, Integration time: 0.1 s PTTBSA, when excited at 420 nm, shows an emission peak near 640 nm. PTTBSA is anionic in nature and attaches with the cationic components/residue present in the water. As PTTBSA attaches to the cationic residue, the emission peak of PTTBSA near 640 nm (when excited at 420 nm) gets attenuated. The degree of attenuation is dependent on the morphology of the cationic residues and their charge densities. This attenuation of the tracer emission spectra can be used as an index of the cationic residue.

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

EXPERIMENTAL DETAILS

Example 1

All the stock solutions were prepared in Milli-Q water.

Experiment 1: Preparation of Fluorescent Tracer Stock Solution 1 mg of 4,4',4",4'''-(Porphine-5,10,15,20-tetrayl) tetrakis benzenesulfonic acid (fluorescent tracer) and 10 ml of Milli-Q water were mixed to generate a 100 ppm stock solution of the fluorescent tracer in a borosil bottle. The mixture was shaken vigorously. The bottle of the stock solution was covered using aluminium foil to ensure that light did not enter into the tracer solution. This minimized any potential photo bleaching of tracer solution. The stock solution was used for two weeks before making a new batch.

Experiment 2: Preparation of Chemical Stock Solution

1% stock solutions of various samples, such as Chemical D (30/70 mole ratio DADMAC/AcAm copolymer), Chemical E (35/65 mole ratio of DMAEA.MCQ/AcAm copolymer), Chemical F (Epichlorohydrin-dimethylamine based polymer), Chemical G (diallyil-dimethyl ammonium chloride based polymer), Chemical B (50/30/20 mole ratio of DMAEA.BCQ/DMAEA.MCQ/AcAm copolymer) Chemical H (diallyil-dimethyl ammonium chloride based polymer), and Chemical I (Poly triethanol amine methyl chloride quaternary), were made by injecting 100 μl of each chemical in 10 ml Milli-Q (MQ) water. The various chemicals D, E, F, G, B, H, I and A were used for the preparation of the samples comprising the commonly used cationic coagulants and flocculants. The samples were blended in water by applying a VWR Vortex mixer for about 4 minutes, followed by shaking for about 2 hours before testing. Chemical stock solutions were prepared every day before the start of the experiment. The details regarding various chemicals used for this study are provided in table 1.

was inserted into the cell of the spectrofluorometer. Fluorescence spectra were measured using the following setting:
  a. Excitation wavelength: 420 nm, Slit width: 2.5 nm
  b. Emission spectra wavelength range: 500-700 nm, Slit width: 2.5 nm
  c. Detector setting: Detector type S (S1), measuring unit CPS, Integration time: 0.1 s Experiment 5: Preparation of Synthetic Reverse Emulsion Oil-in-water synthetic reverse emulsions were prepared in the laboratory. 250 ml Milli-Q water was poured in a Borosil bottle. Crude oil was shaken for about 5 minutes on an

TABLE 1

Details of the chemicals used

| Identifier | Chemical Group | Detailed comments | Charge density (meq/g) | Mole charge |
|---|---|---|---|---|
| Chemical A | N-allkyl dimethyl benzyl ammonium chloride | 18 wt % active polymer in product | | |
| Chemical B | Acrylic polymer (cationic) | DMAEA•BCQ/DMAEA•MCQ/AcAm at mole ratio (50/30/20) terpolymer @ 20 wt % active polymer in the product | 3.9 | 80% cationic |
| Chemical C | Dithiocarbamate | Anionic neutralizer | | |
| Chemical D | Polyamine quat. | DADMAC/AcAm (30/70 mole ratio) copolymer @ 20 wt % active polymer in product | 3.0 | 30% cationic |
| Chemical E | Acrylic polymer (cationic) | DMAEA•MCQ/AcAm at mole ratio (35/65 mole ratio), 20 wt % active polymer in product | 3.1 | 35% cationic |
| Chemical F | Epichlorohydrin-dimethylamine based polymer | 55 wt % active polymer in product | 7.3 | |
| Chemical G | Diallyl dimethyl ammonium chloride based polymer | 18 wt % active polymer in product | 6.2 | |
| Chemical H | Diallyl dimethyl ammonium chloride based polymer | 20 wt % active polymer in product | 6.2 | |
| Chemical I | Poly (triethanol amine) methyl chloride quat | 30 wt % active polymer in product | 5 | |

Experiment 3: Bottle Test for Mixing the Tracer with the Sample 50 ml Milli-Q water was poured in a prescription bottle. The target sample was injected at selected dosage using a micropipette. The bottle was shaken gently about 100 times to ensure efficient mixing. The tracer was added from the stock solution at the target dosage followed by about 100 gentle shakes for efficient mixing to obtain the target sample.

Experiment 4: Fluorescence Spectroscopy

A Horiba Jobin Yvon Fluoromax-4 Spectrofluorometer was employed for fluorescence spectroscopy. The quartz crystal cuvette was cleaned carefully using Milli-Q water and acetone. The cuvette was rinsed with the target sample twice. About 4 ml of target sample was injected into the cuvette using disposable droppers. The outer surface of the cuvette was wiped carefully using Kim wipes. The cuvette Eberbach lateral shaker at high speed (240 rpm) for uniform mixing. The homogeneous crude oil was injected into the water according to the target oil-in-water concentration using a micropipette (e.g. if the target OIW is 100 ppm, 25 micro liter oil was added to 250 ml water). The bottle was capped. The bottle was placed in the tray of the lateral shaker and shaken at a speed of 240 rpm for about 30 minutes. After about 30 minutes, the shaker was stopped and the bottle was rotated to an angle of 180° and shaken repeatedly for about 30 minutes. The shaker was stopped after about 30 minutes. The uniform shaking generated a stable dispersion of oil in water.

Experiment 6: Measuring Oil-in-Water Using Turner TD500D Oil-in-Water Meter

Oil-in-water value was measured using a Turner TD500D oil-in-water meter. Calibration solutions of target oil at specific concentrations in cyclohexane were prepared and the Turner TD500D instrument was calibrated against the target solutions. Cyclohexane was used for extraction of oil from oil in water emulsion solution (target oil). A 10 ml sample of oil-in-water reverse emulsion was collected in a 15 ml vial followed by 1 ml cyclohexane addition. The vial was capped and shaken vigorously to ensure uniform mixing of the cyclohexane into the oil-in-water reverse emulsion, which extracted the oil from the water into cyclohexane. The vial was allowed to stand for about 2 hours to ensure proper separation of the water and the organic phase. The oil extracted in the organic phase was procured using a 2 ml syringe. The procured sample was placed into a mini cuvette and the fluorescence signal of the sample was measured. Based on the calibration sample data, the instrument measured the oil-in-water value from the target sample.

Experiment 7: Detecting Cationic Species in Water

Various stock solutions of samples (10 ppm) prepared in experiment 2 were tested. A pre-determined volume of fluorescent tracer was added from a stock solution to a known volume of sample solution as prepared in experiment 1. The amount of tracer addition was controlled as per the required tracer to cation ratio, e.g. 25 µl of tracer stock solution (of concentration 100 ppm) was added to 50 mL of Mili-Q water containing different cationic species, each at a concentration of 10 ppm, yielding a tracer to cationic species ratio of 1:200 w/w. A HORIBA FluoroMax fluorescence spectrophotometer was used for measuring emission spectra of the fluorescent tracer. Excitation was maintained at 420 nm while emission spectra data was measured from 500 nm to 700 nm. The fluorescent tracer emission peak showed up in the range of 640 nm to 660 nm, with a dependence on the presence or absence of cationic species. Fluorescence intensity increased with fluorescent tracer concentration in the absence of a cationic species as expected, but a key feature of detection was the attenuation of fluorescence signal in the presence of cationic species, which was observed at all concentrations of the fluorescent tracer. The addition of about 0.005 ppm fluorescent tracer (cationic species to fluorescent tracer ratio 200:1) yielded significant attenuation and this ratio was maintained for cationic species detection initially.

Figure 2:
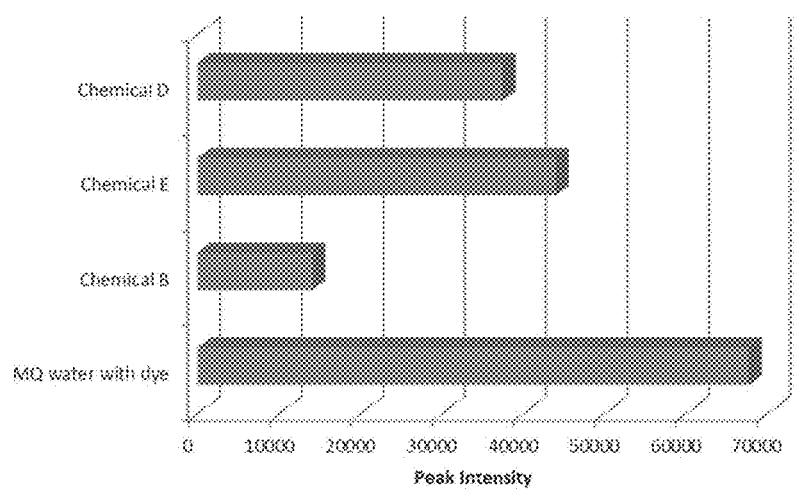
FIG. 2 illustrates the PTTBSA tracer emission spectra using various cationic flocculants.

It was observed that the PTTBSA tracer emission peak in Milli-Q water was close to 70000 CPS while in the presence of other cationic species, PTTBSA tracer emission peak showed a varied amount of attenuation. The difference in attenuation between the baseline of around 70000 CPS to around 14000 CPS (for Chemicals B, E and D), as seen in FIG. 2 can be attributed to the surface charge density of the target cationic species and hence acts as an index for differentiation of target species. Hence FIG. 2 provides examples of detecting various cationic flocculants using the method as disclosed in the present disclosure.

Figure 3:
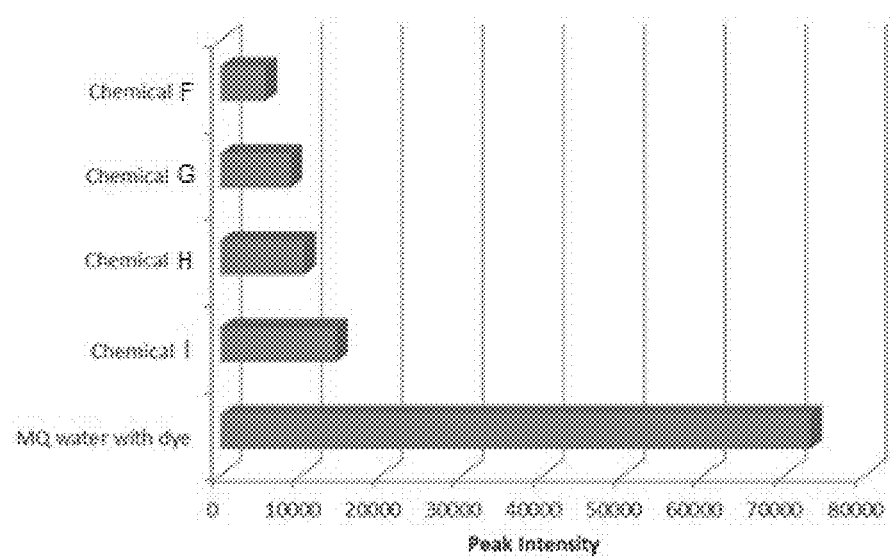
FIG. 3 illustrates the PTTBSA tracer emission spectra using various cationic coagulants.
Figure 4:
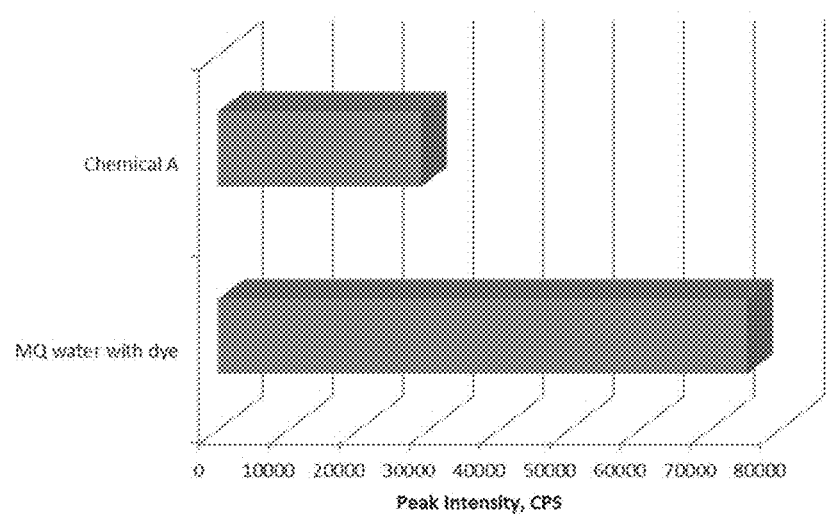
FIG. 4 illustrates the PTTBSA tracer emission spectra with Chemical A.

Similar observation is found for cationic coagulants which are shown in FIG. 3. Hence FIG. 3 provides examples of detecting various cationic coagulants using the method of the present disclosure. FIG. 4 shows the detection of Chemical A which can be component of a typical corrosion inhibitor and a biocide. Hence FIG. 4 provides example of detecting a corrosion inhibitor and biocide using the method as disclosed in the present disclosure.

Figure 5:
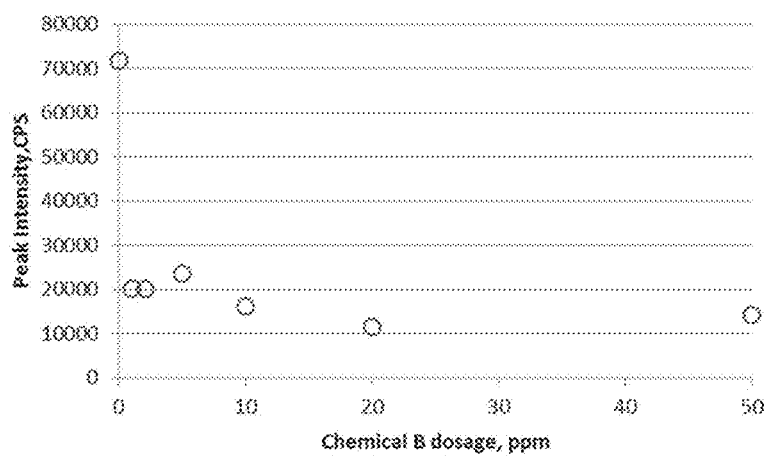
FIG. 5 illustrates the emission spectra of Chemical B for different concentrations/dosage.

The strong interaction between PTTBSA tracer (anionic fluorescent dye) and the cationic species permits the detection of a trace quantity of residual cationic species in water by dosing a fixed quantity of the fluorescent tracer to it. As Chemical B is one of the commonly used cationic flocculants in the oilfields for water treatment, a focused study was carried out for detecting Chemical B in water using the method described in the present disclosure. A dosage response of Chemical B was done in Milli-Q water. FIG. 5 shows that there was a steep decrease in fluorescence intensity when the Chemical B concentration in water ranges from 1 ppm to 5 ppm as compared to the absence of Chemical B. Above 5 ppm the fluorescence of the fluorescent tracer showed a gradual decrease and eventually reached a plateau above 20 ppm. The observed behavior of fluorescence was due to the quenching of the fluorescence of the anionic fluorescent tracer by neutralization with the residual cationic species (Chemical B).

Experiment 8: Effect of Salinity

The electrostatic interaction between the fluorescent tracer and the cationic species which drives the attenuation of the emission peak can be altered in the presence of salt. Increasing salt concentration decreases the Debye length in aqueous environments and the electrostatic interactions are screened. As a consequence, the effective charge density of the cationic species in the water is reduced and the attenuation of fluorescence signal of the anionic fluorescent tracer by charge neutralization might also be reduced.

Figure 6:
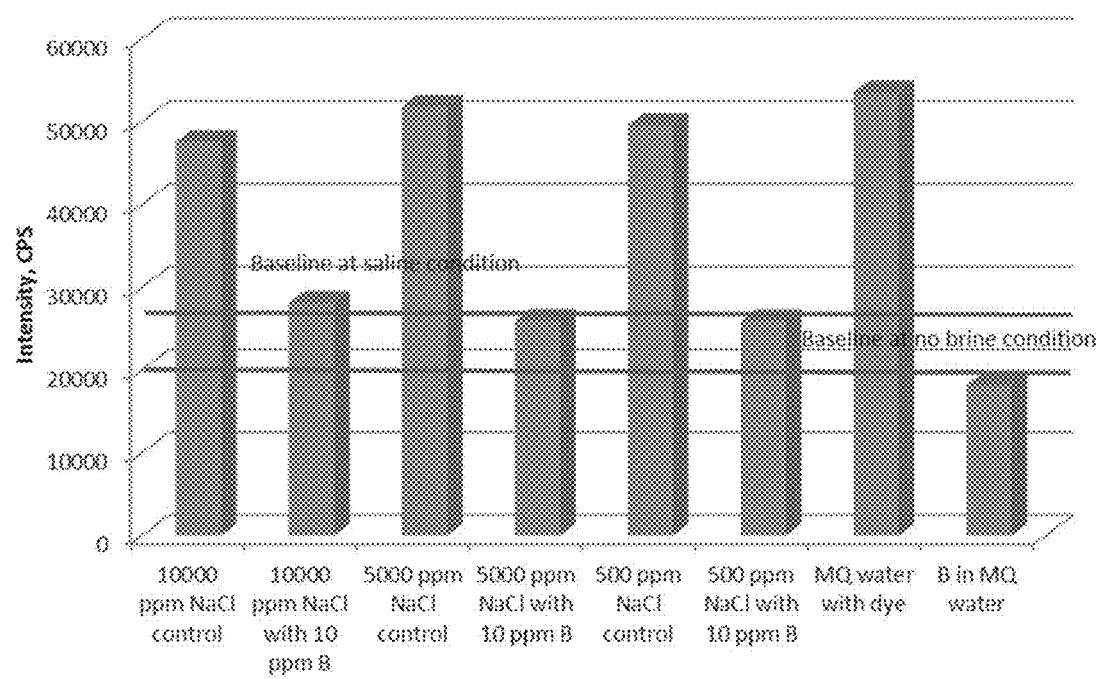
FIG. 6 illustrates the effect of salinity on fluorescence attenuation of PTTBSA tracer.

The effect of salinity on fluorescent tracer attenuation was studied with 10 ppm Chemical B in three different brine conditions (500 ppm, 5000 ppm and 10000 ppm of NaCl). Control runs were performed with the brine solutions without any cationic species addition. FIG. 6 shows the effect of salinity on fluorescence attenuation of PTTBSA tracer (anionic fluorescent dye).

It was observed that in the presence of NaCl alone, i.e. in the absence of cationic species, the signal intensity with the dye remained nearly constant at 47000 CPS to 55000 CPS irrespective of NaCl concentration. This eliminates any possibility of the interaction between the salinity and dye alone. It was also observed that in the presence of cationic species, the fluorescence intensity decreases from 55000 CPS (0 ppm cationic species) to 28000 CPS (10 ppm concentration cationic species) at 500 ppm NaCl, the signal attenuation decreased and the dye emission peak increased.

At a fixed concentration of 10 ppm cationic species, higher saline conditions (5000 ppm and 10000 ppm NaCl concentrations) did not affect the fluorescent tracer emission intensity, which remained constant at 28000 CPS. Therefore, it can be concluded that there is a change in electrostatic forces when salinity changes from 0 to 500 ppm NaCl concentration. However, from 500 ppm to 10000 ppm NaCl concentration range, there is no significant change in the emission peak (49580 CPS, 51840 CPS, and 47560 CPS). Hence, in a practical scenario, the developed method is robust enough to withstand the expected levels of salinity change in the field. The fluorescent tracer emission intensity in Milli-Q water as shown in FIG. 6 is around 55000 CPS, which is different from the other experimental data (near 70000 CPS). This difference in fluorescent intensity at the same fluorescent tracer concentration is attributed to the photo-bleaching of the PTTBSA tracer (anionic fluorescent dye) with aging (since the difference is observed even when no residual cationic species is present). Using a freshly prepared stock solution of fluorescent tracer can avoid the effect of photo-bleaching.

Experiment 9—Effect of Oil Presence in OIW Reverse Emulsions

Figure 7:
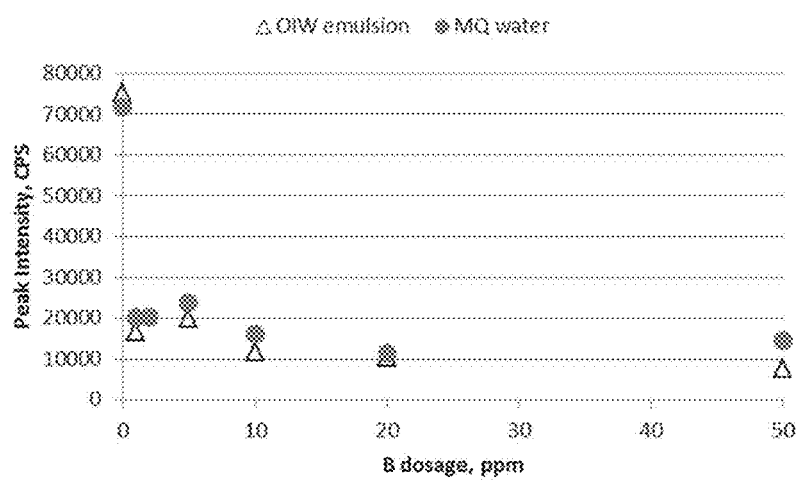
FIG. 7 illustrates Chemical B dosage response in target OIW reverse emulsion.

Oil is known to cause interference in fluorescence signal. Hence, control studies were done on Chemical B dosage response on a target oil-in-water reverse emulsion (target OIW 30 ppm) of a Gulf-of Mexico crude oil in Milli-Q water. As shown in FIG. 7, it was observed that for a 30 ppm target OIW reverse emulsion (as shown as Δ in FIG. 7), the attenuation of fluorescent emission intensity due to the presence of Chemical B followed a trend similar to that observed in Milli-Q water (as shown as ● in FIG. 7). As the maximum limit of the OIW must remain below 30 ppm to comply with environmental regulations, the method of the present disclosure can be effective in detecting the presence of residual cationic species in overboard discharge water. This detection of residual cationic species is very useful to comply with environmental regulations that are in place to minimize toxicity to aquatic life caused by cationic polymers.

Experiment 10: Data Analysis Technique to Minimize Interference from the Oil in Fluorescent Signal To understand the effect of interference coming from oil in the emission range of interest, several synthetic OIW reverse emulsions were generated in the laboratory with varying amount of OIW. Control runs were performed without any cationic species addition. Two sets of emission spectra were compared for these blank reverse emulsions. The first set constituted emission spectra without the addition of any fluorescent tracer. The second set constituted emission spectra with the selected fluorescent tracer. It was found that the emission spectra without the addition of any fluorescent tracer can be considered as a baseline. Subtracting the baseline data points from the second set (emission spectra with the selected fluorescent tracer) can provide data with minimal interference from the oil.

Figure 8:
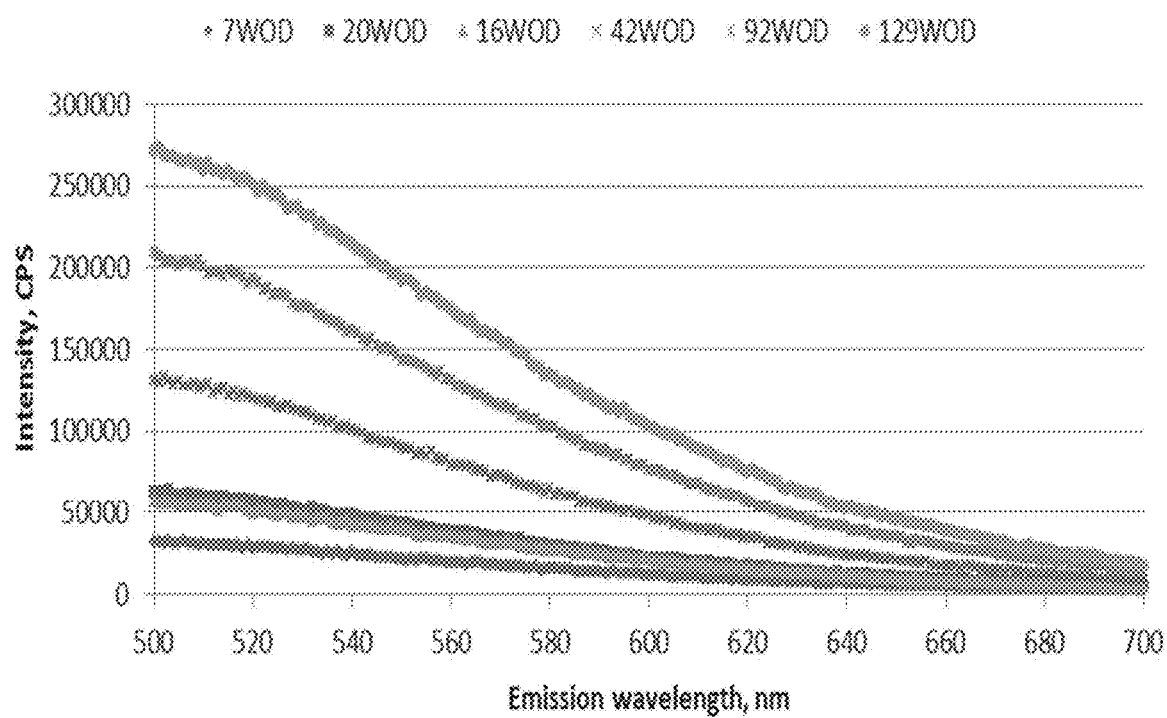
FIG. 8 illustrates fluorescence interference from oil as a baseline.
Figure 9:
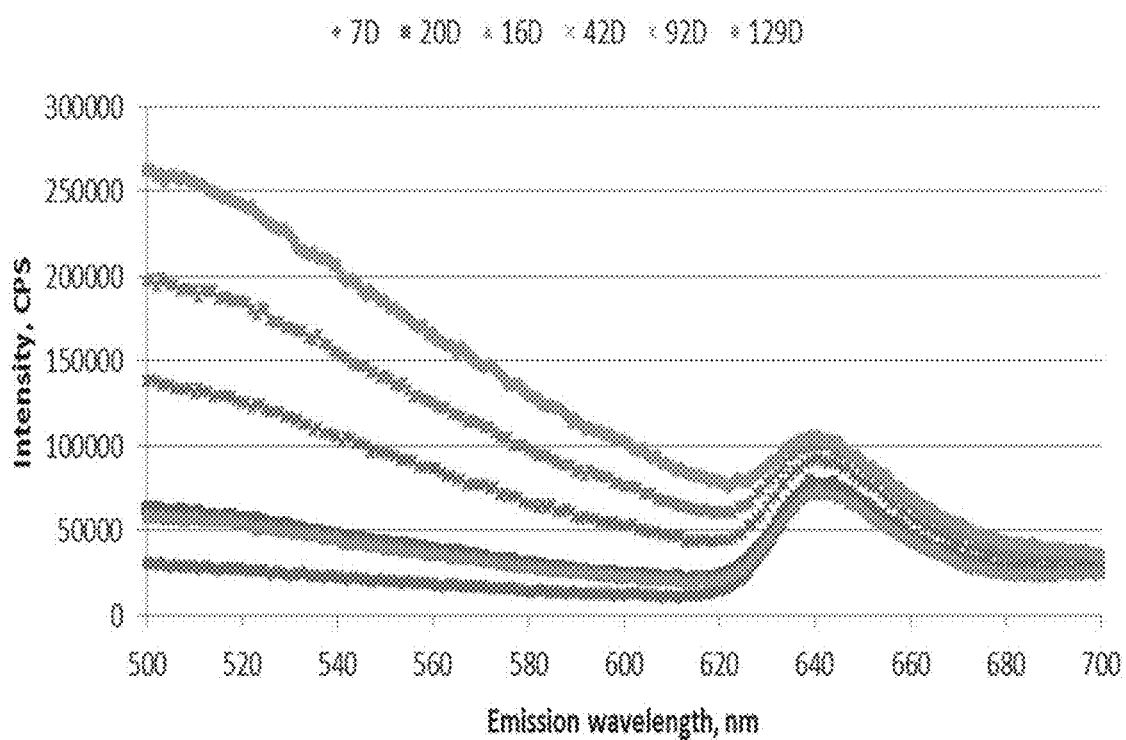
FIG. 9 illustrates emission data, combining oil interference and fluorescence from the tracer.
Figure 10:
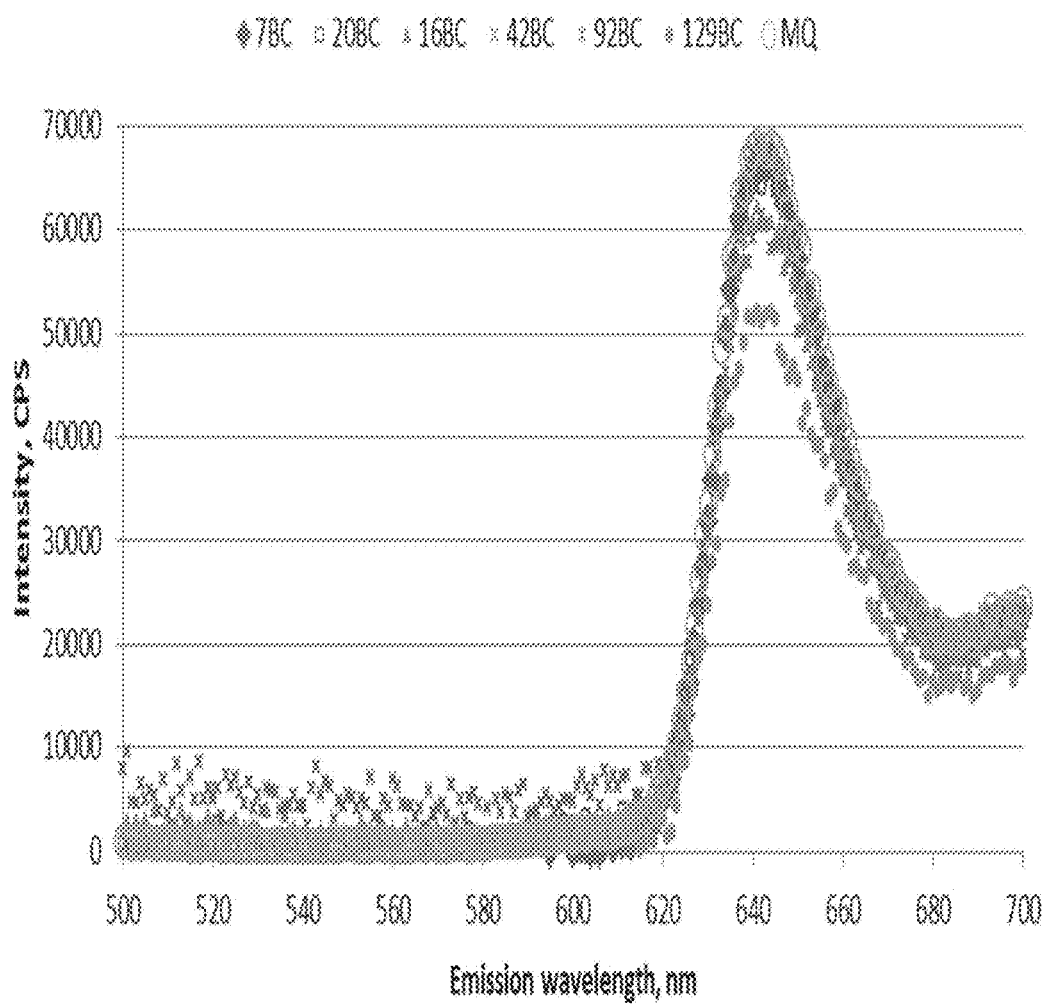
FIG. 10 illustrates the baseline corrected emission data.

FIG. 8 represents the interference coming from oil. In FIG. 8, the numerical value represents the OIW value measured and WOD refers to control run without the presence of dye. FIG. 9 represents the emission data coming from the oil and the dye. In FIG. 9, the numeric value represents the measured OIW value and D refers to the addition of the dye. FIG. 10 represents the baseline corrected data as discussed earlier. In FIG. 10, the numeric value represents the OIW measured and BC refers to a baseline corrected value. FIG. 7 shows the effect of oil in OIW reverse emulsions. Although no significant peak showed up near the 640 nm to 655 nm range, which is the fluorescent tracer emission spectra range, the interference causes increase in the fluorescent tracer emission peak as shown in FIG. 8. The base line correction as mentioned here showed dye peak data to remain in the range of 60000 to 70000 CPS (in 7-92 ppm OIW range) which should be within reasonable accuracy given the uncertainties associated with the error limit of the fluorescent detector, experimental error of sample preparation and fluorescent tracer addition and photo-bleaching of the fluorescent tracer during the experimental process.

Figure 11:
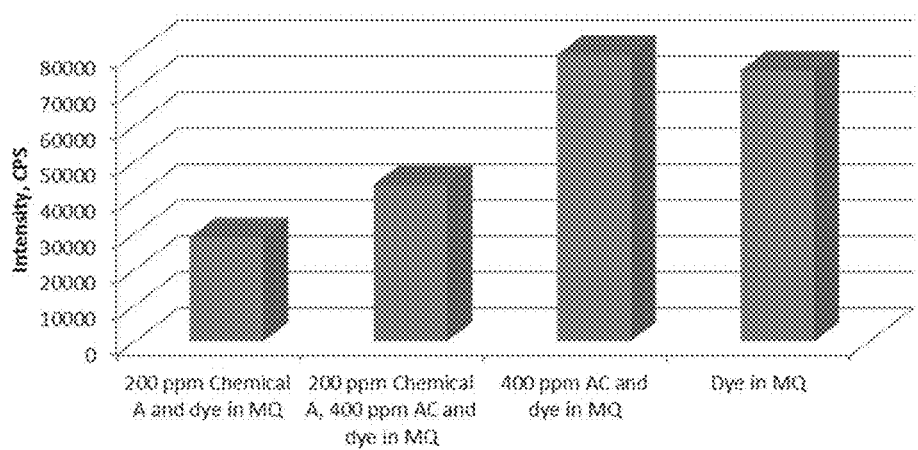
FIG. 11 illustrates the detection of change in charge functionality of Chemical A using a suitable anionic species.

Experiment 11: A Quick Method to Detect Loss of Charge Functionalities in Chemicals and a Concept of Charge Neutralization Using Different Neutralizers Charge functionalities in chemicals often dictate their performance in multiple products like corrosion inhibitors (CI), deoilers/water clarifiers, emulsion breakers, biocides, etc., catering to various OFC (oilfield chemicals) and WPS applications (Water and Process Services). Customers often face the challenges of reduced efficiencies of such chemicals over time. While a change in process condition often drives a change in performance of recommended chemicals, loss of charge functionalities of the chemical due to improper storage and contamination can be another factor that influences such a change in product performance. A systematic study was employed by using the method of the present disclosure to detect loss of charge functionalities of a typical corrosion inhibitor (CI) such as Chemical A (N-alkyl dimethyl benzyl ammonium chloride). Chemical A (200 ppm in Milli-Q water) shows significant attenuation of the dye's fluorescence intensity from 72000 CPS in the case of blank to 23000 CPS in the presence of Chemical A, as shown in FIG. 4 and FIG. 11. When 400 ppm of an anionic coagulant (AC) was added in the Milli-Q water containing 200 ppm Chemical A, an increase in dye emission peak was noticed to 40000 CPS. As the anionic coagulant (Chemical C) neutralizes the cationic groups of the CI, a lesser number of such cationic functionalities are available to neutralize the anionic dye. This causes a lower degree of attenuation of the dye's emission intensity, and as a result an increase in its peak intensity is observed from 23000 CPS to 40000 CPS.

A control run was carried out with the same dosage of Chemical A in Milli-Q water and an anionic coagulant in Milli-Q water. The data showed no change in dye emission peak intensity in the presence of Chemical A in Milli-Q water as compared to the dye emission peak intensity of anionic coagulant in Milli-Q water. The control run data validated that the anionic species used for this study did not influence attenuation of the dye signal. A comparison of the control run and target neutralization of the CI with Chemical A suggests that if a foreign species is added into Milli-Q water containing 200 ppm of Chemical A, it changes the nature of Chemical A in terms of its interaction with the tracer. As a result of a change in the tracer, attenuation is observed. Accidental injection of such a foreign species in a cationic chemical can lead to chemical contamination and nullify its charge functionalities at a customer site. Prolonged storage can also cause loss of cationic charge functionalities of a product. The data presented in FIG. 11 suggest that the method of the present disclosure is sensitive to such a change in the charge functionalities of the cationic species. Hence, the method of the present disclosure can be used as a quick method to analyze any change in cationic charge functionalities of a target chemical and thus any change in the performance of charge functionalities of cationic species can be rightly attributed to either product contamination or a probable change in field condition.

Figure 12:
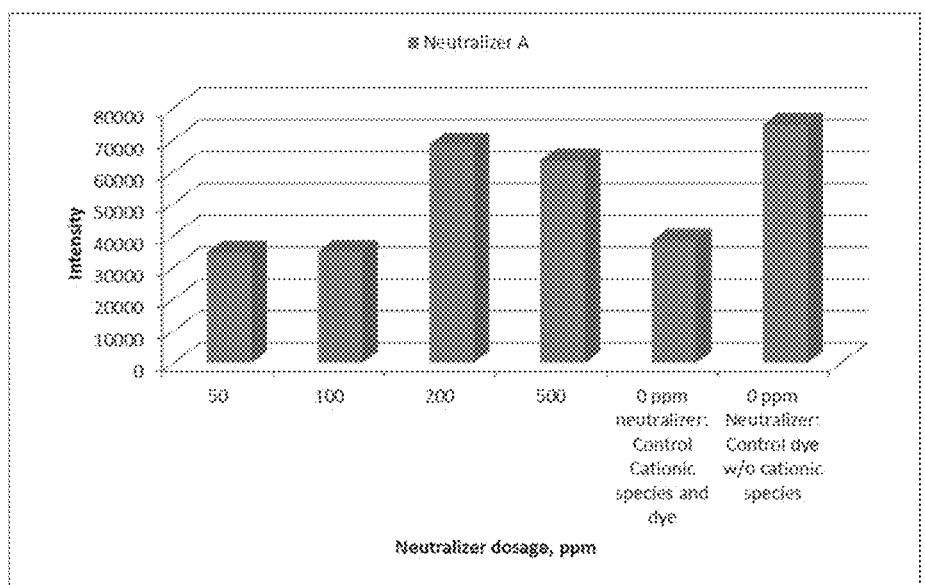
FIG. 12 illustrates the detection of change in charge functionality of Chemical A using citric acid
Figure 13:
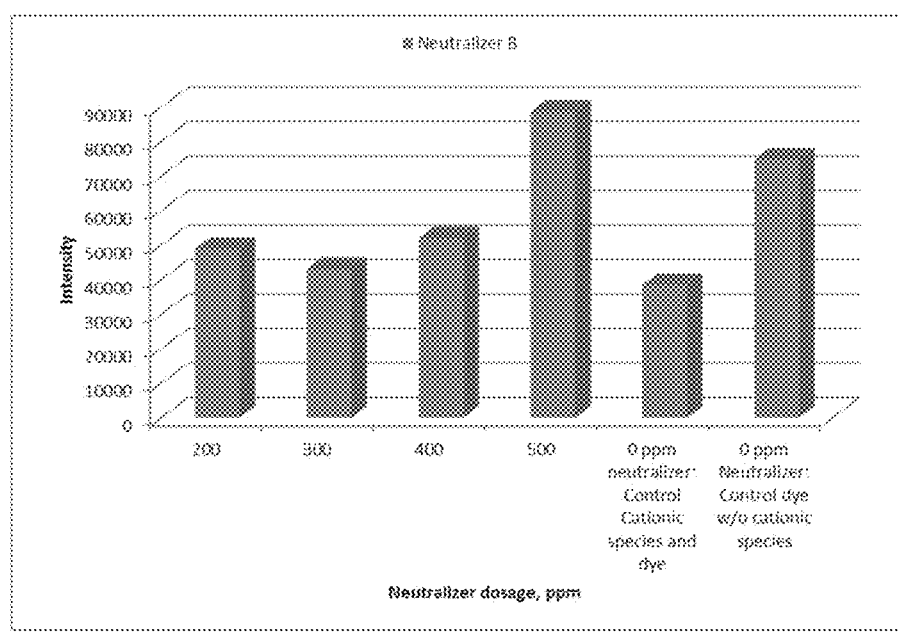
FIG. 13 illustrates the detection of change in charge functionality of Chemical A using tartaric acid

The data presented in FIG. 12 and FIG. 13 show the charge neutralization of Chemical A using two other commercially available neutralizers (A=citric acid and B=tartaric acid). These two sets of tests were carried out in presence of 2000 ppm NaCl brine while the tests described in FIG. 11 were carried out in deionized water. Two control runs (in absence of the neutralizers) were carried out with the dye in the presence and absence of 200 ppm Chemical A. Optimal neutralizer dosage could be identified based on the intensity profile of these control runs. The study of the effect of the three neutralizers (Dithiocarbamate (Chemical C), Citric acid, and Tartaric acid) over Chemical A suggests that the optimal neutralizer dosage can vary depending on the target species and the neutralizer being used. In the actual situation, presence of suspended solid particles, salinity, and pH would also affect the optimal neutralizer dosage. The method described in the invention would be able to identify an effective neutralizer and predict its optimal dosage.

It should be noted that various salt of these organic acids (citrates, tartrates) could be applied as effective neutralizers. Various other organic carboxylates can also be effectively used as a charge neutralizer. The invention described herein would be able to screen a suitable neutralizer.

The methods of the present disclosure have several technical advantages over the existing art. Such advantages include, but are not limited to, detecting and controlling a cationic species present in a water stream by using a fluorescent tracer and optimizing the dosage of an anionic neutralizer; providing a water stream which is safe for the environment; providing an effective method even in the presence of salt and oil in the water stream; minimizing the error in data due to oil interference; and providing a simple and cost effective method for detecting and controlling cationic species in the water stream.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results. While certain embodiments of the inventions have been described, these embodiments have been presented by way of example only, and are not intended to limit the scope of the inventions. Variations or modifications to the formulation of this invention, within the scope of the invention, may occur to those skilled in the art upon reviewing the disclosure herein. Such variations or modifications are well within the spirit of this invention.

The numerical values given for various physical parameters, dimensions, and quantities are only approximate values and it is envisaged that the values higher than the numerical value assigned to the physical parameters, dimensions and quantities fall within the scope of the invention unless there is a statement in the specification to the contrary.

While considerable emphasis has been placed herein on the specific features of certain embodiments, it will be appreciated that many additional features can be added and that many changes can be made in the disclosed embodiments without departing from the principles of the disclosure. These and other changes to the embodiments explicitly disclosed herein will be apparent to those skilled in the art, whereby it is to be distinctly understood that the foregoing descriptive matter is to be interpreted merely as illustrative and not limiting.

Additionally, any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

What is claimed is:

1. A method for detecting and controlling an amount of a cationic species in a water stream, comprising:
   a. drawing a water sample from said water stream;
   b. adding a pre-determined quantity of at least one fluorescent tracer to said water sample to form a solution comprising a complex, wherein said at least one fluorescent tracer is (4,4',4'',4'''-(Porphine-5,10,15,20-tetrayl) tetrakis (benzenesulfonic acid);
   c. measuring a fluorescence emission spectra of said complex in a range of about 500 nm to about 700 nm when excited at about 420 nm and detecting the presence or absence of the cationic species in the complex of said solution based on an attenuation of an emission peak and a shift of the emission peak in a range of about 640 nm to about 655 nm;
   d. detecting a quantity of the cationic species in said water sample;
   e. adding an amount of an anionic neutralizer proportional to the quantity of the cationic species detected in step (d) to said water stream to obtain a water stream with the desired level of the cationic species; and
   f. optionally repeating the steps (a) to (e) for controlling the amount of the cationic species in said water stream below a threshold level.

2. The method as claimed in claim 1, wherein said step of detecting the quantity of the cationic species in said water sample is carried out by measuring a fluorescence intensity and/or a fluorescence peak of said water sample after mixing a predetermined quantity of the at least one fluorescent tracer in increasing mass of water in the sample to obtain one or more mixtures, each mixture comprising a complex of the at least one fluorescent tracer and the cationic species and measuring the fluorescence intensity of the complex present in the mixture until the fluorescence intensity of the mixture reaches a steady state.

3. The method as claimed in claim 1, wherein said step of detecting the quantity of the cationic species in the water sample is carried out by measuring a fluorescence intensity and/or a fluorescence peak of the water sample by mixing a predetermined volume of the water sample with an increasing quantity of the at least one fluorescent tracer to obtain one or more mixtures, each mixture comprising a complex of the at least one fluorescent tracer and the cationic species and measuring the fluorescence intensity of the complex present in the mixture until the fluorescence intensity of the mixture reaches a steady state.

4. The method as claimed in claim 1, wherein said cationic species is selected from the group consisting of a coagulant, a flocculant, a water clarifier, a biocide, a corrosion inhibitor, and any combination thereof.

5. The method as claimed in claim 1, wherein said threshold level of the cationic species in the water stream ranges from about 1 ppm to about 50 ppm.

6. The method as claimed in claim 1, wherein the step of measuring the fluorescence emission spectra in method step (c) comprises a pre-step of correcting a baseline of the absorbance spectra to nullify an effect of a spectral interfering component.

7. The method as claimed in claim 1, wherein a mass ratio of the cationic species to the at least one fluorescent tracer ranges from about 100:1 to about 250:1.

8. The method as claimed in claim 1, wherein the pre-determined quantity of the at least one fluorescent tracer ranges from about 5 ppb to about 10 ppb.

9. The method as claimed in claim 1, wherein said at least one fluorescent tracer is an anionic fluorescent dye.

10. The method as claimed in claim 1, wherein step (a) comprises a pre-step of treating the water stream using a treating agent, wherein the treating agent is at least one selected from the group consisting of a biocide, a flocculant, a corrosion inhibitor, a coagulant and a water clarifier.

11. The method as claimed in claim 1, wherein said anionic neutralizer is at least one selected from the group consisting of a coagulant and a flocculant.

12. The method as claimed in claim 1, wherein said anionic neutralizer comprises a dithiocarbamate.

13. The method as claimed in claim 1, wherein the water stream is an oil field water stream or an industrial waste water stream.

14. The method as claimed in claim 1, wherein the method prevents fouling of a piece of equipment in contact with the water stream.

* * * * *

UNITED STATES PATENT AND TRADEMARK OFFICE
CERTIFICATE OF CORRECTION

PATENT NO. : 10,544,054 B2
APPLICATION NO. : 15/878641
DATED : January 28, 2020
INVENTOR(S) : Saugata Gon et al.

Page 1 of 1

It is certified that error appears in the above-identified patent and that said Letters Patent is hereby corrected as shown below:

On the Title Page

Column 2, Line 2, Item (56), "Other Publications" please delete "-Methoxphenyl)" and insert -- -Methoxyphenyl)--.

Column 2, Line 7, Item (56), "Other Publications" please delete "withd-andf-electron" and insert --with d- and f- electron--.

Signed and Sealed this
Fourteenth Day of April, 2020

Andrei Iancu
*Director of the United States Patent and Trademark Office*